United States Patent [19]
Kleemiss et al.

[11] Patent Number: 5,728,873
[45] Date of Patent: Mar. 17, 1998

[54] PROCESS FOR THE PREPARATION OF CYCLOPROPANAMINE

[75] Inventors: Wolfgang Kleemiss, Haltern; Thomas Kalz, Herne, both of Germany

[73] Assignee: Huels Aktiengesellschaft, Marl, Germany

[21] Appl. No.: 663,989

[22] Filed: Jun. 14, 1996

[30] Foreign Application Priority Data

Jun. 30, 1995 [DE] Germany .................. 195 23 868.0

[51] Int. Cl.⁶ .................................................. C07C 209/56
[52] U.S. Cl. ......................... 564/1; 564/414; 564/448; 564/488
[58] Field of Search ........................... 564/1, 414, 448, 564/488

[56] References Cited

U.S. PATENT DOCUMENTS

| | | | |
|---|---|---|---|
| 3,711,549 | 1/1973 | Phillips et al. | 260/563 R |
| 4,590,292 | 5/1986 | Blackwell et al. | 560/124 |
| 5,032,687 | 7/1991 | Diehl et al. | 564/1 |

*Primary Examiner*—Brian M. Burn
*Attorney, Agent, or Firm*—Oblon, Spivak, McClelland, Maier & Neustadt, P.C.

[57] ABSTRACT

A process for the preparation of cyclopropanamine by Hofmann degradation of cyclopropanecarboxamide, comprising the following steps:

(1) suspending cyclopropanecarboxamide, either (A) in 1.1 to 4 mol of sodium hydroxide, in solution whose concentration is 10 to 50%, per mol of amide, or (B) in a sparing amount of water, (2) adding 1 to 1.5 mol of hypochlorite, per mol of amide, from a 5 to 15% strength hypochlorite solution at a temperature of 0° to 20° C., (3) adding 1.1 to 4 mol of sodium hydroxide, in solution whose concentration is 10 to 50%, per mol of amide, in the case where a suspension has been formed according to step (1)(B), (4) reacting the amide, hypochlorite, and sodium hydroxide for 10 to 60 minutes to form a homogeneous reaction mixture, (5) continuously passing the homogeneous reaction mixture through a tubular reactor at a temperature of 45° to 260° C., (6) feeding the reaction output from the tubular reactor into a distillation column and keeping it under reflux with water, wherein cyclopropanamine is distilled off.

17 Claims, 1 Drawing Sheet

PROCESS FOR THE PREPARATION OF CYCLOPROPANAMINE

BACKGROUND OF THE INVENTION

1. Field of the Invention

The present invention relates to a novel process for the preparation of cyclopropanamine by Hofmann degradation of cyclopropanecarboxamide.

2. Description of the Prior Art

The Hofmann degradation of cyclopropanecarboxamide to form cyclopropanamine is known in principle. Thus, it is described in DE-A 19 39 759 that the amide is first reacted with a concentrated hypochlorite solution in aqueous solution at 0° C. The mixture is allowed to post-react at this temperature and then an excess of sodium hydroxide solution is added. The mixture is then heated to 45° to 50° C. The cyclopropanamine is then obtained by steam distillation.

In EP-B 0 205 403 it is emphasized that the reaction mixture of cyclopropanecarboxamide, hypochlorite and sodium hydroxide solution has a certain stability only at 0° to 10° C. At higher temperatures the Hofmann degradation proceeds spontaneously with great liberation of heat. This fact makes industrial realization of the Hofmann degradation virtually impossible under discontinuous conditions.

In the above-mentioned European Patent, a process is therefore described in which the amide is continuously pumped in a mixture with the hypochlorite which is kept at low temperature, together with sodium hydroxide solution, into a distillation column in which water boils under reflux.

In this manner, the highly exothermic step of the Hofmann degradation—decarboxylation of the chlorinated amide to give the amine—proceeds virtually in the distillation column, while at the same time the cyclopropanamine can be distilled off at the top of the column.

However, the strong dilution effect, which occurs due to the large amount of the water boiling under reflux in the column, leads to a retardation of the reaction so that the decarboxylation to the cyclopropanamine only proceeds completely in the distillation bottom phase.

Back-mixing therefore occurs, which, as is also described in DE-A 23 28 757, leads to side reactions.

As is described in EP-B 0 367 010, very good yields of cyclopropanamine are obtained if the cyclopropanecarboxamide is reacted in the form of an aqueous solution, preferably in water, with the hypochlorite solution at 10° to 20° C. The reaction mixture is then introduced into an excess of a concentrated alkali metal hydroxide solution, the reaction temperature being between 10° and 35° C. By introducing the solution of the chlorinated amide into the sodium hydroxide solution excess, the highly exothermic hydrolysis with elimination of $CO_2$ can be controlled by the rate of the addition. Therefore, the selectivity of the Hofmann degradation is said not to suffer because of the above-described back-mixing conditions.

A considerable disadvantage of the process is the extremely low space/time yield of the reaction which occurs because the amide is used in the form of an aqueous solution (at most approximately 12% strength in amide). Even the highly dilute hypochlorite solution (at most 14 to 15% strength) causes a poor space/time yield.

A further disadvantage of the process is that the cyclopropanamine, after the Hofmann degradation, must be discontinuously distilled from the reaction mixture, which again decreases the space/time yield.

In another process variant (EP-B 0 393 350) the cyclopropanecarboxamide in the form of a solution, preferably an aqueous solution, is brought into contact with a mixture of hypochlorite and sodium hydroxide solution, preferably continuously, at a temperature of 45° to 260° C. In this variant, chlorination and decarboxylation reactions proceed together in a short time. In the continuous procedure, the high heat of reaction can be removed in a controlled manner. The amine is then produced discontinuously by distillation in a yield of >90%.

Here also, the space/time yield suffers on the one hand from the highly dilute cyclopropanecarboxamide solution and on the other hand from the fact that the reaction product after the reaction is distilled discontinuously.

SUMMARY OF THE INVENTION

The object was therefore to find a process by which cyclopropanamine can be prepared in high purity from cyclopropanecarboxamide, and in which a maximum space/time yield and continuous removal of the heat of reaction are ensured.

The object is achieved according to the invention by providing the cyclopropanecarboxamide in suspension form and conducting the Hofmann degradation under certain specified conditions.

DESCRIPTION OF THE PREFERRED EMBODIMENTS

Figures 1A, 1B:
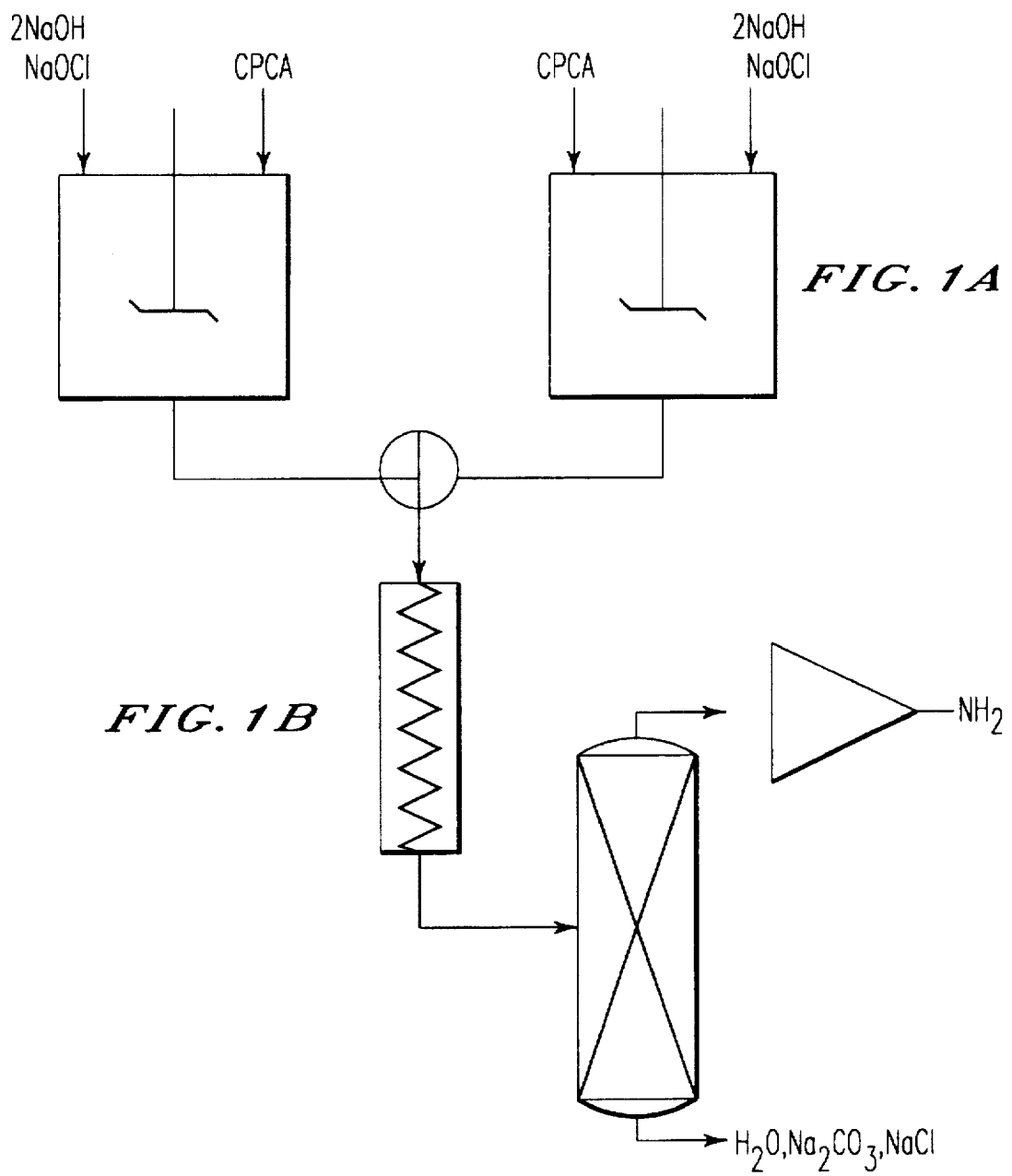
FIG. 1 illustrates, in block diagram form, an embodiment of the inventive process disclosed herein using alternately two stirred reactors.

In one variant (Variant A) the cyclopropanecarboxamide is suspended at a temperature of 0° to 20° C., preferably 10° to 15° C., in an excess necessary for the Hofmann degradation of 1.1 to 4 mol, preferably 2 to 3 mol, per mol of amide, of sodium hydroxide in solution of 10 to 50%, preferably 20 to 40%, concentration. 1 to 1.5 mol of a 5 to 15% strength, preferably 10 to 14% strength, hypochlorite solution is then metered into the suspension in such a way that the reaction temperature does not leave the range between 0° and 20° C., preferably 10° to 15° C.

After a reaction time period of 10 to 60 min, preferably 20 to 40 min, the now homogeneous reaction mixture is continuously passed through a tubular reactor, the temperature of which is 45° to 260° C., preferably 60° to 150° C. The residence time is between 0.2 and 20 min, but preferably between 0.5 and 5 min, in order, on the one hand, to achieve complete conversion and, on the other hand, to ensure a maximum space/time yield of the reaction. However, the residence time is more preferably in the range 0.5 to 3 min, particularly preferably 0.7 to 1.5 min, because very good space/time yields are obtained thereby.

In another variant (Variant B), the cyclopropanecarboxamide is suspended at a temperature of 0° to 20° C., preferably 10° to 15° C., in water. Hypochlorite solution in the same amounts and under the same conditions as in Variant A is metered into the suspension. Sodium hydroxide solution, in the same strength and in the same amounts as in Variant A, is then added to the suspension. After a reaction time period of 10 to 60 min, preferably 20 to 40 min, the now homogeneous reaction mixture is continuously passed through a tubular reactor, and the remainder of the process is carried out like Variant A. Alternatively, the sodium hydroxide solution may be continuously added to the suspension during the above reaction time period.

The reaction output is then fed into a distillation column in which water is kept under reflux and is discontinuously, or continuously, preferably continuously, worked up, i.e., obtained by distillation. In the case of continuous workup, the cyclopropanamine can be continuously taken off at the top of the column, while the inorganic salt byproducts pass into the bottom phase of the distillation apparatus. The bottom phase can in turn be pumped off continuously. In this manner, cyclopropanamine is obtained in a yield of >90% having a purity of >99%.

In order to prevent excessive amounts of unstable reaction mixtures from arising, the cyclopropanecarboxamide can expediently be chlorinated semicontinuously, alternately in two stirred reactors. While the completely reacted chlorination mixture of the first reactor is being pumped into the heated tubular reactor, the next chlorination is begun in the second stirred reactor, etc.

Surprisingly, the cyclopropanecarboxamide can also be chlorinated in the presence of the sodium hydroxide solution excess (Variant A) without side reactions occurring.

Optionally, cyclopropanecarboxamide can also be chlorinated in such a way that the amide, suspended in a sparing amount of water, is introduced and the hypochlorite solution is added so that a temperature of 0° to 20° C. can be set (Variant B).

Only subsequently is the sodium hydroxide solution mixed with the chlorination mixture and then pumped through the tubular reactor at a temperature of 45° to 260° C. Workup by distillation of the cyclopropanamine can then proceed again continuously.

Continuously carrying out the hydrolytic decarboxylation at 45° to 260° C. allows for controlling the high heat of reaction released in a short time.

Surprisingly, carrying out the decarboxylation of the chlorinated amide continuously further ensures good selectivity of the reaction, no side-reactions of relatively great extent occurring.

Having generally described this invention, a further understanding can be obtained by reference to certain specific examples which are provided herein for purposes of illustration only and are not intended to be limiting unless otherwise specified.

The apparatus used according to the invention in the following examples is depicted in FIG. 1. Examples 1 and 2 are examples of Variant A. Example 3 is an example of Variant B.

EXAMPLE 1 a) Beginning with stirred reactor vessel A, 42.6 g (0.5 mol) of cyclopropanecarboxamide (CPCA) suspended in 200 g (1 mol) of 20% strength sodium hydroxide solution are alternately introduced each time at 10° to 15° C. into two separate, coolable 1 liter stirred reactor vessels A and B (time requirement approximately 10 min). 373 g (0.5 mol) of 10% strength sodium hypochlorite solution are metered into the suspension with stirring in such a way that the temperature of 15° C. is not exceeded (time requirement approximately 10 min). During a further stirring period of approximately 20 min, the reaction mixture becomes homogeneous.

b) In the course of approximately 45 min, the solution (volume=740 ml) is now pumped through a tubular reactor (volume=19 ml) heated to 80° C., so that a residence time of about 1.5 min at 80° C. results. The still hot tubular reactor output is metered into the middle of a column in which water is kept under reflux. After the contents of the stirred reactor A have been virtually completely metered into the distillation apparatus, the cyclopropanamine is begun to be distilled off at a reflux ratio of reflux: take off=5:1. The salt-containing distillation bottom phase is likewise continuously pumped off.

c) While the first solution is being metered, 42.6 g (0.5 mol) of cyclopropanecarboxamide suspended in 200 g (1 mol) of 20% strength sodium hydroxide solution are introduced into the stirred reactor vessel B at 10° to 15° C. (time requirement: approximately 10 min). 373 g (0.5 mol) of 10% strength sodium hypochlorite solution are metered into the suspension in such a way that the reaction temperature of 15° C. is not exceeded (time requirement: approximately 10 min.). During the further stirring time of approximately 20 min, the reaction mixture becomes homogeneous.

d) After the stirred reactor A has been emptied, the three-way cock is now switched over so that the homogeneous contents of the reactor B are metered through the tubular reactor. During this time, 42.6 g (0.5 mol) of cyclopropanecarboxamide are chlorinated again in stirred reactor A.

In this manner, a total of 170.4 g (2 mol) of cyclopropanecarboxamide are converted to cyclopropanamine.

In the continuous distillation, 93 g (81%) of cyclopropanamine are obtained (purity: >99%). 24.7 g (12%) of 54% strength aqueous cyclopropanamine are obtained as a second fraction. The total yield of cyclopropanamine is therefore 93%.

EXAMPLE 2 a) 42.6 g (0.5 mol) of cyclopropanecarboxamide suspended in 200 g (1 mol) of 20% strength sodium hydroxide solution are introduced into the stirred vessel A at 15° to 20° C. In the course of approximately 10 min, 279 g (0.5 mol) of 13.4% strength sodium hypochlorite solution are metered into the suspension, such that the reaction temperature does not exceed 20° C. The mixture is further stirred for approximately 20 min at 15° to 20° C. and then the homogeneous reaction mixture is begun to be metered at a rate of 25.5 g/min (21.2 ml/min) through the tubular reactor (volume=15 ml) heated to 80° C. (residence time at 80° C. of 0.7 min). The tubular reactor output then passes into the center of the column in which water is kept under reflux. The continuous production of cyclopropanamine proceeds as previously described in Example 1. The reflux ratio chosen is reflux: take off=3:1.

b) When the contents of the stirred reactor A are begun to be metered through the tubular reactor, another 42.6 g (0.5 mol) of cyclopropanecarboxamide are chlorinated in stirred reactor B as in stirred reactor A.

c) When the stirred reactor A has been pumped empty, by switching over the three-way cock, the contents of reactor B are pumped through the tubular reactor.

In this manner, a total of 426 g (5 mol) of cyclopropanecarboxamide are degraded to cyclopropanamine according to Hofmann.

At a top temperature of 50° C., 254.8 g of 99.6% pure (0.2% water) cyclopropanamine are obtained. This amount corresponds to a yield of 89%. At a top temperature of 50° to 100° C., 77 g of 18% pure (81% water) cyclopropanamine (4.9%) are then obtained.

The total yield of cyclopropanamine is thus 93.9%.

EXAMPLE 3 a) 42.6 g (0.5 mol) of cyclopropanecarboxamide suspended in 50 g of water are introduced into stirred vessel A at 15° to 20° C. In the course of approximately 10 min, 238.1 g (0.5 mol) of 13.2% strength sodium hypochlorite solution are metered into the suspension, such that the reaction temperature does not exceed 20° C. The mixture is further stirred for approximately 15 min at 15° to 20° C. and then in the course of 5 min, 200 g (1 mol) of 20% strength sodium hydroxide solution are added. The mixture temperature is maintained so that it does not exceed 20° C. The homogeneous reaction mixture is then metered at a rate of 26 g/min (21.2 ml/min) through the tubular reactor (volume=15 ml) heated to 90° C. The residence time is thus 0.7 min. The reactor output then passes into the center of the column in which water is kept under reflux. The continuous production of cyclopropanamine is performed as previously described in Example 1. The reflux ratio chosen is reflux: take off=3:1.

b) When the contents of the stirred reactor A are begun to be metered through the tubular reactor, another 42.6 g (0.5 mol) of cyclopropanecarboxamide are chlorinated in stirred reactor B as in stirred reactor A.

c) When stirred reactor A has been pumped empty, by switching over the three-way cock, the contents of reactor B are pumped through the tubular reactor.

In this manner, a total of 426 g (5 mol) of cyclopropanecarboxamide are degraded to cyclopropanamine according to Hofmann. At a top temperature of 49° to 51° C., 262.7 g of 99.6% pure (0.3% water) cyclopropanamine are obtained. This amount corresponds to a yield of 91.6%. At a top temperature of 51° to 100° C., 64.9 g of 2.6% pure (97.2% water) cyclopropanamine (0.6%) are obtained. The total yield of cyclopropanamine is thus 92.2%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A process for the preparation of cyclopropanamine by Hofmann degradation of cyclopropanecarboxamide, comprising the following steps:

(1) suspending cyclopropanecarboxamide, either (A) in 1.1 to 4 mol of sodium hydroxide, in solution whose concentration is 10 to 50%, per mol of amide, or (B) in a sparing amount of water, (2) adding 1 to 1.5 mol of hypochlorite, per mol of amide, from a 5 to 15% strength hypochlorite solution at a temperature of 0° to 20° C., (3) adding 1.1 to 4 mol of sodium hydroxide, in solution whose concentration is 10 to 50%, per mol of amide, in the case where a suspension has been formed according to step (1)(B), (4) reacting the amide, hypochlorite, and sodium hydroxide for 10 to 60 minutes to form a homogeneous reaction mixture, (5) continuously passing the homogeneous reaction mixture through a tubular reactor at a temperature of 45° to 260° C., (6) feeding the reaction output from the tubular reactor into a distillation column and keeping it under reflux with water, wherein cyclopropanamine is distilled off.

2. The process according to claim 1, wherein the sodium hydroxide is added in an amount of 2 to 3 mol, in a solution whose concentration is 20 to 40%, per mol of amide, the hypochlorite is added from a 10 to 14% strength hypochlorite solution at a temperature of 10° to 15° C., the reaction time in step (4) is 20 to 40 min, and the tubular reactor is at a temperature of 60° to 150° C.

3. The process according to claim 1, wherein the reaction is carried out at 0° to 20° C. semicontinuously alternately in two stirred reactors.

4. The process according to claim 2, wherein the reaction is carried out at 0° to 20° C. semicontinuously alternately in two stirred reactors.

5. The process according to claim 1, wherein the reaction output is continuously fed into the distillation column in which water boils under reflux.

6. The process according to claim 2, wherein the reaction output is continuously fed into the distillation column in which water boils under reflux.

7. The process according to claim 3, wherein the reaction output is continuously fed into the distillation column in which water boils under reflux.

8. The process according to claim 1, wherein the cyclopropanamine is continuously distilled off at the top of the column and a solution of salt byproducts is continuously pumped from the bottom phase.

9. The process according to claim 2, wherein the cyclopropanamine is continuously distilled off at the top of the column and a solution of salt by-products is continuously pumped from the bottom phase.

10. The process according to claim 3, wherein the cyclopropanamine is continuously distilled off at the top of the column and a solution of salt byproducts is continuously pumped from the bottom phase.

11. The process according to claim 4, wherein the cyclopropanamine is continuously distilled off at the top of the column and a solution of salt byproducts is continuously pumped from the bottom phase.

12. The process according to claim 1, wherein the residence time in the tubular reactor is between 0.2 and 20 minutes.

13. The process according to claim 1, wherein the residence time in the tubular reactor is between 0.5 and 5 minutes.

14. The process according to claim 1, wherein the residence time in the tubular reactor is between 0.5 and 3 minutes.

15. The process according to claim 1, wherein the residence time in the tubular reactor is between 0.7 and 1.5 minutes.

16. The process according to claim 1, wherein step (1)(A) is carried out.

17. The process according to claim 1, wherein step (1)(B) and step (3) are carried out.

* * * * *